(12) United States Patent
Morello

(10) Patent No.: US 6,231,819 B1
(45) Date of Patent: May 15, 2001

(54) DEVICE FOR SUPPORTING INSTRUMENTS IN AN ENCLOSURE, IN PARTICULAR A DECONTAMINATION ENCLOSURE. A CORRESPONDING ENCLOSURE

(75) Inventor: Gérard Morello, Hardricourt (FR)

(73) Assignee: T.S.R. SA, Clichy (FR)

( * ) Notice: Subject to any disclaimer, the term of this patent is extended or adjusted under 35 U.S.C. 154(b) by 0 days.

(21) Appl. No.: 09/198,577

(22) Filed: Nov. 24, 1998

(51) Int. Cl.[7] .................................................. B01J 19/08
(52) U.S. Cl. .................................... 422/186.3; 422/186.15
(58) Field of Search ............................ 422/186.3, 186.15

(56) References Cited

U.S. PATENT DOCUMENTS

| | | | |
|---|---|---|---|
| 4,698,206 | * 10/1987 | Nevin | 422/24 |
| 5,288,467 | 2/1994 | Biermaier . | |
| 5,534,221 | 7/1996 | Hillebrenner et al. . | |

FOREIGN PATENT DOCUMENTS

| | | |
|---|---|---|
| 2090141 | 7/1982 | (GB) . |
| 6 0209-248 | * 2/1984 | (JP) . |
| 9406478 | 3/1994 | (WO) . |

* cited by examiner

Primary Examiner—Kathryn Gorgos
Assistant Examiner—J. Maisano
(74) Attorney, Agent, or Firm—Birch, Stewart, Kolasch & Birch, LLP

(57) ABSTRACT

A device for supporting instruments in an enclosure, in particular a decontamination enclosure, the enclosure being defined by a bottom, at least one vertical side wall, and a top cover, each instrument having an active portion and a connection portion in the form of a cable, the device comprising a bracket extending substantially perpendicularly to the vertical side wall inside the top portion of the enclosure, said bracket having a plurality of suspension members each of which is designed to co-operate with a portion of cable close to the active portion of an instrument.

8 Claims, 2 Drawing Sheets

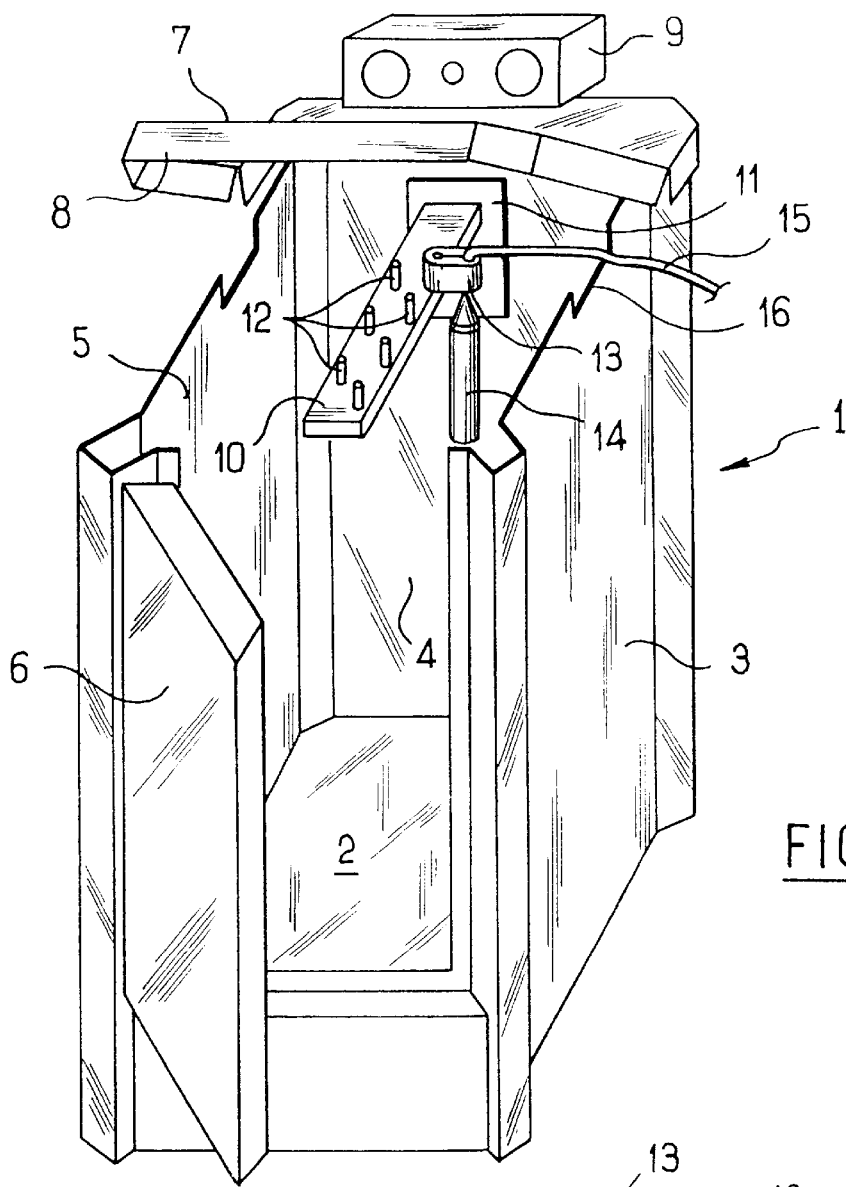
FIG_1
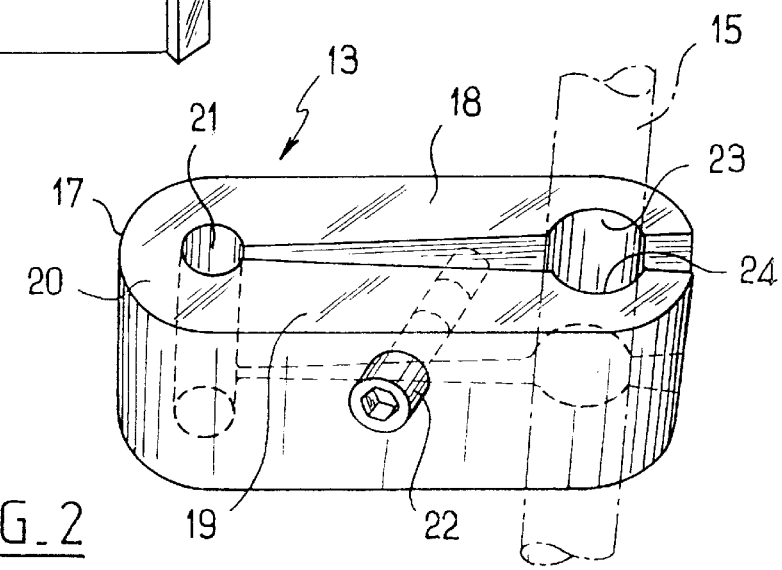
FIG_2

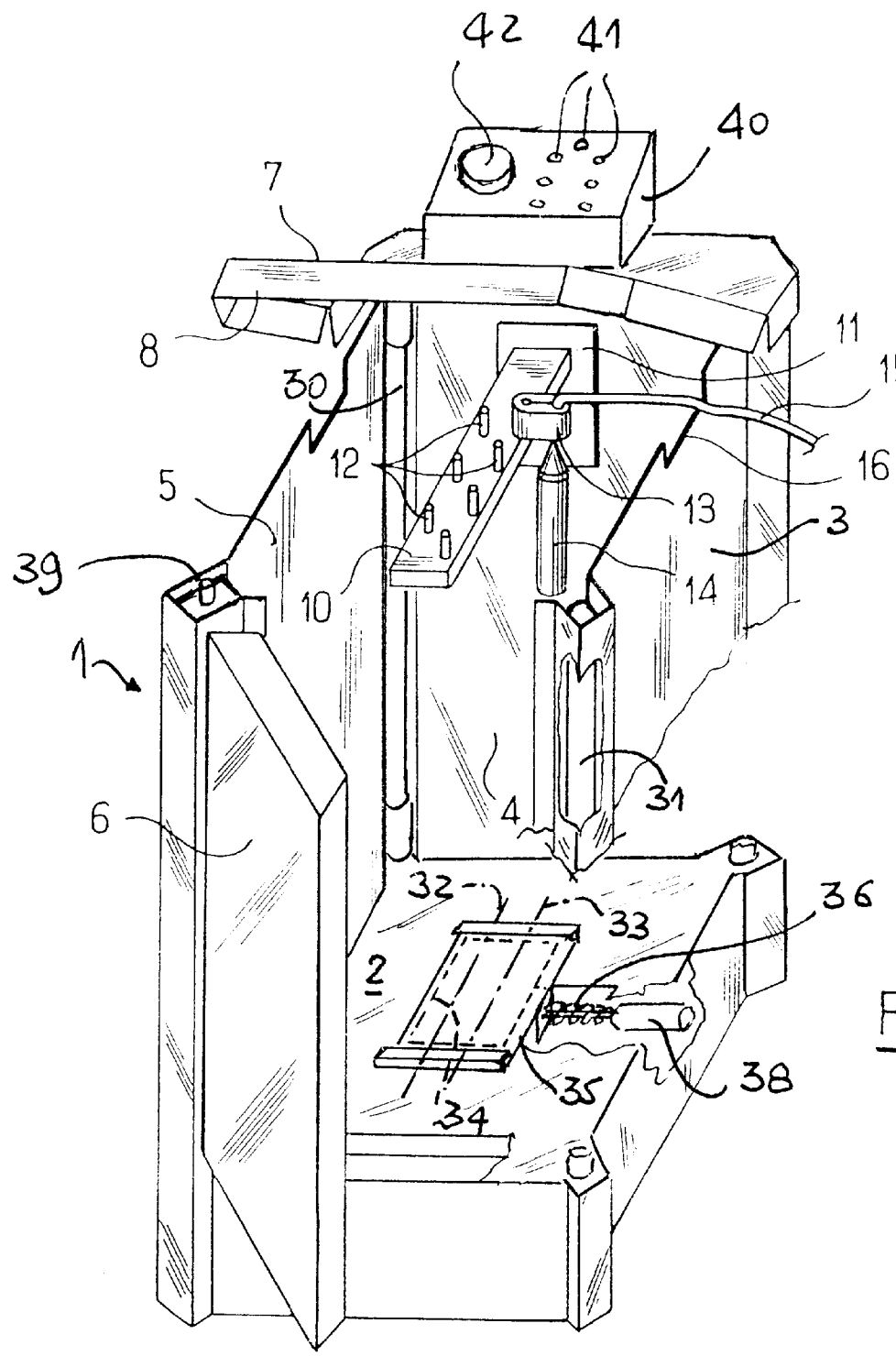
FIG_3

DEVICE FOR SUPPORTING INSTRUMENTS IN AN ENCLOSURE, IN PARTICULAR A DECONTAMINATION ENCLOSURE. A CORRESPONDING ENCLOSURE

The present invention relates to a device for supporting instruments, in particular medical instruments, in an enclosure that is designed to decontaminate them and to keep them decontaminated until they are used.

BACKGROUND OF THE INVENTION

It is known to house medical or surgical instruments in a closed space within which a decontamination atmosphere is organized either by means of an agent inserted into the enclosure, or by means of germicidal radiation emitted into the enclosure, or else by a combination of both.

In the particular case of instruments that are elongate, e.g. echographic probes, the instruments are integrally formed with leads for connecting them to external appliances for feeding them with electricity and for making use of signals emitted by the active portion of the appliance. The combined length of the active portion and the lead of the instrument can be non-negligible.

It has been necessary to find a way of housing them easily in a decontamination enclosure using means that can accommodate their various lengths and their various diameters.

OBJECTS AND SUMMARY OF THE INVENTION

To solve this problem, the present invention proposes a support device that is particularly simple and advantageous, whereby the active portion of an appliance is placed in optimum manner within the enclosure so as to be exposed most effectively to the germicidal agents by contact or by radiation, while the lead portion is disposed in such a manner as to avoid hindering treatment of the active portion.

To this end, the invention therefore provides a support device for supporting instruments in an enclosure, in particular a decontamination enclosure, the enclosure being defined by a bottom, at least one vertical side wall, and a top cover, each instrument having an active portion and a connection portion in the form of a cable, the device comprising a bracket extending substantially perpendicularly to the side vertical wall inside the top portion of the enclosure, said bracket having a plurality of suspension members each being designed to co-operate with a portion of cable adjacent to the active portion of the instrument.

In a particular embodiment, each suspension member comprises a finger installed on a top surface of the bracket and a suspension clamp having two branches that are united at one end which is provided with an orifice for being engaged on the above-mentioned finger, with the free ends of the branches of the clamp being shaped so as to be tightened onto the portion of the connection cable that is adjacent to the active portion of the instrument. The clamp is then put into place on the instrument, and more precisely on its cable, while they are outside the enclosure and is then engaged via its pierced end on one of the fingers included on the bracket. The other end of the clamp which is clamped onto the cable of the instrument is cantilevered out sideways from the bracket so that instruments are spaced apart from one another. The active portion of each instrument then hangs down inside the enclosure where it is properly exposed to the germicidal agents, while the connection cable is situated above the clamp so as to be capable of being held by a secondary support member close to the side wall of the enclosure.

The branches of the clamp may be subjected to a resilient force urging them towards each other so as to tighten automatically onto the cable placed between them. It is also possible to provide a drive member between the branches for the purpose of moving them apart or towards each other so as to be able to clamp the cable between them positively with a controlled amount of force, and to be able to release said force. A screw linking together the branches can perform this function.

The secondary support member for the cable of each instrument can be constituted simply, merely by the top edge of the side wall of the enclosure, and preferably by the bottom of a notch formed in the top portion thereof. The cables of the instruments are then kept substantially horizontal in the vicinity of the cover of the enclosure so as to avoid needlessly occupying the space inside the enclosure in which the active portion of each instrument is received.

BRIEF DESCRIPTION OF THE DRAWINGS

Other characteristics and advantages of the invention appear from the following description of an embodiment given purely by way of indication.

Reference is made to the accompanying drawings, in which:

FIG. 1 is a simplified overall view of a decontamination enclosure fitted with a support device of the invention;

FIG. 2 is a detail view of the clamp used in the FIG. 1 support device; and

FIG. 3 is an overall view similar to FIG. 1 of a decontamination enclosure implementing sources of germicidal radiation.

MORE DETAILED DESCRIPTION

The enclosure 1 shown in FIG. 1 comprises a bottom 2, and four side walls 3, 4, 5, and 6, with the side wall 6 forming an outwardly opening front door. A cover 7 having downwardly-extending margins 8 gives access to the inside volume of the enclosure from above and constitutes simple means for keeping the door 6 in its closed state. The enclosure has a control panel 9.

The side wall 4 that is remote from the front door 6 carries a bracket 10 via a mounting plate 11. The bracket is situated in the top portion of the enclosure and extends over the bottom 2, being vertically above it inside the enclosure. It carries a plurality of fingers 12 forming vertical pegs directed towards the cover 7.

In the figure, one of these pegs is shown fitted with a suspension member 13 as described in greater detail with reference to FIG. 2 for suspending a medical, surgical, or diagnostic instrument 14, e.g. an echographic probe 14, which is extended in conventional manner by a connection cable 15.

The cable 15 extends substantially horizontally from above the suspension member 13 in the top portion of the enclosure to a notch 16 formed in the top portion of the side wall 3. Beyond the notch, the cable leaves the enclosure. It can be seen in FIG. 1 that the suspension member 13 has one of its ends fitted on a finger 12 and is cantilevered out sideways from the bracket 10 so that each instrument 14 hangs down away from the bracket and thus away from other instruments that might be suspended from the other side thereof.

Naturally, the invention also covers variants that are not shown. For example, the bracket 10 may have orifices for engaging fingers that are carried by the respective suspension members 13. Also for example, the bracket could be fitted on its sides with resilient clips each having jaws between which it is possible to engage the cable of an instrument. It is also possible to provide lateral notches and to fix annular rings on the cables to form suspension abutments for the corresponding instruments. Each notch could be in the form of a slot leading to an eye, and each ring could have a shoulder so that on being installed in a notch lateral locking takes place preventing the suspended instrument from escaping from the notch (e.g. when installing an adjacent instrument).

From FIG. 1, it can be seen that the connection cable portion of each instrument is confined in the top portion of the enclosure where it extends in a substantially horizontal position. The cover leaves clearance between its downwardly-extending rim 8 and the outside of the side wall, so the cable portions outside the enclosure do not impede closing the enclosure. If it is necessary to have sealing, that can be provided at the notch and the corresponding zone of the cover by complementary means (e.g. deformable gaskets).

In FIG. 2, the suspension member 13 shown is in the form of a clamp 17 having two thick branches 18 and 19 which join at an end 20 where they form an orifice 21 of diameter approximately equal to that of a peg 12 and of axial length sufficient to secure the clamp properly to the bracket. The two branches 18 and 19 can be moved towards each other or apart from each other by a screw 22 (without significantly altering the diameter of the orifice 21), with said branches being provided with respective part-cylindrical recesses 23 and 24 for fitting around the outside surface of a cable 15 and for clamping thereto.

FIG. 3 shows most of the elements described above, and they are given the same references. The enclosure shown in this case is adapted to decontamination by radiation. For this purpose, it is fitted with conventional tubes for emitting ultraviolet radiation. In the example shown, there are six such tubes. Four of them are received in the corners of the enclosure like the tubes 30 and 31, while the last two of them 32 and 33 are received at the bottom of the enclosure beneath the bottom wall 2 which is provided with a window 34 vertically beneath the bracket 10.

Given the nature of the instruments that are to be decontaminated, it has been found that it is extremely important to subject the ends of their active portions to direct radiation. When the instruments are suspended, said ends face downwards, so the radiation sources must be located in the bottom portion. This disposition nevertheless suffers from the drawback of exposing the bottom tubes to the risk of being broken if one of the suspended instruments were to fall. This risk is real only while the instruments are being put into place or are being removed, since once they are suspended, there is no reason why they should become detached in untimely manner.

That is why the window 34 is provided with a retractable shutter 35 (which may be solid, perforated, a grid, . . . ) which is moved into its window-covering position by a resilient return member (or at least a spring 36). The shutter is also coupled to an actuator 38 (e.g. an electromagnetic actuator) which, when excited, moves the shutter 38 against the effect of the return spring so as to uncover the window. When the cover 7 is closed, thereby acting on a switch 39 for closing the entire electrical circuit, the actuator 38 is powered simultaneously with the tubes 30 to 33. The shutter 35 can be mounted to slide in lateral guides above or beneath the bottom wall 2 of the enclosure, and the spring 36 and the actuator 38 can also be situated beneath said wall. In this context, any other structural disposition that provides the same function forms part of the invention.

On the control panel 40 of the appliance there can be seen lamps 41 for indicating that each of the radiant tubes is in operation and for indicating the position of the shutter 35. A knob 42 forms both an on/off control member for the appliance and a timer member for setting a time period so as to adjust the irradiation time and the excitation time of the actuator 38. At the end of the time period, the tubes are turned off and the shutter 35 closes the opening 34. The bottom tubes are thus protected from a probe dropping both while the probes are being put into place in the enclosure (with its cover open so power to the actuator is off), and while they are being extracted therefrom (with the shutter closing the window as from the end of the time period).

Finally, it should be observed that it is preferable for the position of the shutter 35 to be indicated by means of a lamp 41 that is associated with a position detector rather than with a detector of power being fed to its drive member, so as to be certain that the irradiation is not being masked by a shutter that has remained in its window-closing position in spite of its drive member being appropriately powered.

What is claimed is:

1. A decontamination enclosure comprising a bottom, at least one vertical side wall, and a top cover, for decontaminating at least one instrument having an active portion and a connection portion in the form of a cable integral with said active portion and means for maintaining said instrument in said enclosure wherein said means include a bracket extending substantially perpendicularly to the side vertical wall near said cover, said bracket being provided with at least one suspension member designed to secure a part of said cable adjacent to said active portion and a secondary suspension member for supporting said connection cable and secured to said side wall so as to hold the cable in a substantially horizontal position between said bracket and said side wall.

2. The enclosure of claim 1, wherein said suspension member comprises a finger installed on a top surface of the bracket and a suspension clamp having two branches that are united at one end which is provided with an orifice for being engaged on said finger, with the free ends of the branches of the clamp being shaped so as to be tightened onto said adjacent part of the cable.

3. The enclosure of claim 2, wherein the clamp includes a member for driving its branches to move them toward each other or away from each other.

4. The enclosure of claim 2, wherein the secondary suspension member is constituted by the top edge of the side wall at the bottom of a notch therein.

5. The enclosure of claim 1, wherein at least one emitter of ultraviolet germicidal radiation is situated in a window formed in said bottom wall beneath said bracket of the support device, and wherein the bottom is fitted with a shutter for protecting the emitter, said shutter being movable between a first position in which it covers the window and a second position in which it leaves said window uncovered.

6. The enclosure of claim 5, wherein the shutter is coupled to a member for driving it between said two positions, said member being formed by a resilient element for returning the shutter into its first position and by a drive element which, in its active state, develops a force for displacing the shutter towards its second position against the effect of the resilient return element.

7. The enclosure of claim 6, wherein the drive element is activated by closing the cover of the enclosure, by means of a contact switch.

8. The enclosure of claim 5, including a control panel having an indicator for indicating operation of each radiation emitter and an indicator for displaying the position of the shutter relative to the window.

* * * * *